United States Patent [19]

Johnson

[11] 4,054,600

[45] Oct. 18, 1977

[54] METHOD FOR MAKING AROMATIC BIS(ETHER DICARBOXYLIC ACID)S

[75] Inventor: Donald S. Johnson, Scotia, N.Y.

[73] Assignee: General Electric Company, Schenectady, N.Y.

[21] Appl. No.: 590,877

[22] Filed: June 27, 1975

[51] Int. Cl.$^2$ ............................................. C07C 51/06
[52] U.S. Cl. .......................... 260/520 E; 260/326 A; 260/346.3
[58] Field of Search .................... 260/520 R, 520 E

[56] References Cited

U.S. PATENT DOCUMENTS 3,879,428  4/1975  Heath .............................. 260/520 E
3,965,125  7/1976  Meyers ............................ 260/346.3

Primary Examiner—Norman Morgenstern
Attorney, Agent, or Firm—William A. Teoli; Joseph T. Cohen; Jerome C. Squillaro

[57] ABSTRACT

A method is provided for making aromatic bis(ether dicarboxylic acid)s, such as 2,2-bis[4(3,4-dicarboxyphenoxy)phenyl] propane. The corresponding aromatic bis(etherimide) is hydrolyzed in base to produce a tetraacid salt which is directly acidified with concentrated mineral acid such as sulfuric acid. The resulting aqueous mixture containing a paste is heated to produce the aromatic bis(ether dicarboxylic acid) in ready filterable form.

8 Claims, No Drawings

METHOD FOR MAKING AROMATIC BIS(ETHER DICARBOXYLIC ACID)S

The present invention relates to a method for making certain aromatic bis(ether dicarboxylic acid)s. More particularly, the present invention relates to the base hydrolysis of a bisimide to produce a tetraacid salt followed by acidifying the tetraacid salt with a concentrated mineral acid to produce the corresponding tetraacid in a readily filterable form.

As shown by Heath et al. U.S. Pat. No. 3,879,428, assigned to the same assignee as the present invention, aromatic bis(ether dicarboxylic acid)s are important intermediates for the production of aromatic bis(ether anhydride)s. The aforementioned aromatic bis(ether anhydride)s can be copolymerized with an appropriate aromatic diamine to produce polyetherimides which are useful injection moldable high performance plastic materials.

Prior to the present invention, aromatic bis(ether dicarboxylic acid)s were made by base hydrolyzing the corresponding aromatic bis(etherimide)s to produce the corresponding tetraacid salts. The conversion of tetraacid salt to the corresponding aromatic bis(ether dicarboxylic acid) was achieved by pouring the tetraacid salt into an aqueous excess of mineral acid, such as hydrochloric acid. It was found that the hydrochloride acid was highly corrosive to stainless steel mixing vessels and the buildup of excess aqueous acid mixture rendered the procedure uneconomic.

The present invention is based on the discovery that the direct addition of a concentrated mineral acid such as sulfuric acid to the tetraacid salt base hydrolysis mixture provides for the production of tetraacid, as long as the pH of the resulting mixture is reduced to below 1. However, the tetraacid is generated in the form of a paste which is difficult to filter and work with further. Additionally, it has been found that if the acidification mixture is heated between 80° C to reflux, that the tetraacid is liberated in the form which can be readily recovered by vacuum filtration or centrifugation.

There is provided by the present invention a method for making aromatic bis(ether dicarboxylic acid)s involving 1. hydrolyzing the corresponding aromatic bis(etherimide) with an alkali hydroxide to produce a tetraacid salt base hydrolysis mixture,
2. acidifying the tetraacid salt by pouring the base hydrolysis mixture into a mineral acid solution to produce a tetraacid acidification mixture,
3. effecting the gravity separation of tetraacid from the resulting acidification mixture whereby excess water builds up from the acidification mixture, which method for making aromatic bis(ether dicarboxylic acid) involves the important comprising, 4. acidifying the aromatic bis(ether diacid) salt by directly adding a concentrated mineral acid to the base hydrolysis mixture at a temperature in the range of from about 15° C to 75° C until the pH of the resulting mixture is reduced to less than about 1,
5. heating the resulting mixture to a temperature in the range of between 80° C to reflux, and
6. effecting the separation of the tetraacid from the resulting mixture, whereby excess water buildup from the acidification mixture is substantially reduced and the tetraacid is produced in a ready recoverable form.

The aromatic bis(ether phthalimide)s which can be used in the practice of the invention to produce the aromatic bis(ether dicarboxylic acid)s have the formula, (1)

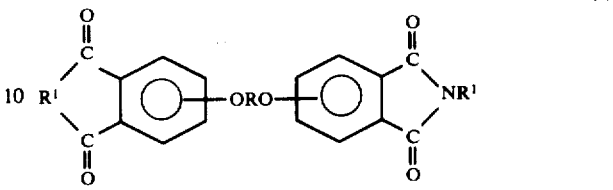

where R is a divalent aromatic radical having from 6–30 carbon atoms and $R^1$ is a monovalent organic radical selected from the class consisting of $C_{(1-8)}$ alkyl radicals and organic radicals having from 6–20 carbon atoms selected from the class consisting of aromatic hydrocarbon radicals and halogenated derivatives thereof.

Radicals included by R are more particularly,

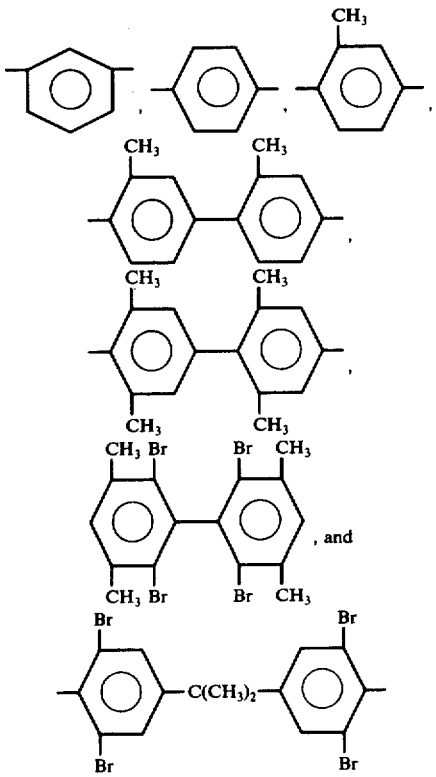

and divalent organic radicals of the general formula

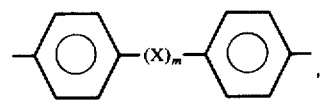

where X is a member selected from the class consisting of divalent radicals of the formulas $-C_yH_{2y}-$,

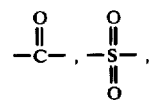

—O—, and —S—, where $m$ is 0 or 1, $y$ is a whole number from 1 to 5.

Radicals included by $R^1$ are, for example, phenyl, tolyl, xylyl, napthyl, chlorophenyl, bromonapthyl, etc., and alkyl radicals such as methyl, ethyl, etc.

In the practice of the invention, the bisimide of formula (1) can be hydrolyzed to the tetraacid salt by refluxing the bisimide in the presence of an alkali hydroxide, for example, sodium hydroxide, etc. Hydrolysis time can vary from 1–24 hours or more, depending upon the reactants, degree of agitation, temperature, etc. The organic amine by product can be removed by standard procedures such as steam distillation, etc. In addition, the rate of hydrolysis is greatly accelerated by carrying the reaction at above atmospheric pressure at temperatures in the range of from 100° C to 220° C.

Neutralization of the tetraacid salt can be effected at temperatures in the range of from about 15° C to about 75° C, and preferably at a temperature in the range of between 15° C to 40° C. A concentrated mineral acid such as sulfuric acid, phosphoric, etc., can be added with stirring to the tetraacid salt hydrolysis mixture. If desired, additional water can be added to maintain the temperature range along with external cooling. When the reaction mixture achieves a pH of about 1 or less, it can be heated to a temperature of about 80° C to reflux to facilitate crystallization. Another technique which can be used in combination with heating is to add a seed crystal to the mixture enabling crystallization to take place at a slightly lower temperature. Stirring and heating of the mixture can be terminated as soon as crystallization has occurred. Filtration of the mixture is preferably effected at a temperature in the range of between 20° C to 40° C to minimize the precipitation of alkali metal sulfate. The tetraacid crystals can then be air dried.

In order that those skilled in the art will be better able to practice the invention, the following examples are given by way of illustration and not by way of limitation. All parts are by weight.

EXAMPLE 1

A mixture of 79 parts of 2,2-bis[4(3,4-dicarboxyphenoxy)-phenyl] propane-bis-N-methyl imide, 79 parts of 50% NaOH and 158 parts of water were stirred and refluxed for 24 hours. The methyl amine evolved was allowed to escape into the atmosphere. The mixture was cooled to room temperature and diluted with an equal volume of water. Sufficient concentrated sulfuric acid having a density of about 1.84 was added slowly to the diluted base solution while it was stirred and maintained at a temperature of about 20° by exterior cooling; the pH of the mixture was reduced to 1 based on variable color pH paper. This produced a pasty mixture, which was heated. At about 95° C, the pasty mixture solidified giving a readily filterable material. The melting point of the product was 203–210 with water evolution which was obtained in quantitative yield based on the weight of bisimide. The product was 2,2-bis[4(3,4-dicarboxyphenoxy)phenyl] propane.

EXAMPLE 2

A mixture of 1 part of 3,3',4,4' tetracarboxy diphenyl ether-bis-N-methyl imide, 1 part 50% NaOH and 2 parts of water were stirred and refluxed for 24 hours. The methyl amine evolved was allowed to escape into the atmosphere. The mixture was then diluted with an equal volume of water and acidified to pH of 1, based on variable color pH paper, by the addition of a sufficient quantity of concentrated sulfuric acid having a density of about 1.84. This resulted in a pasty mixture which was heated. At about 100° C, the mixture solidified giving a readily filterable material. The melting point of the material was 200°–205° C with evolution of $H_2O$. It was obtained in quantitative yield. The product was 3,3',4,4'-tetracarboxy diphenyl ether.

EXAMPLE 3

A mixture of 2 parts of [4(3,4-dicarboxy-phenoxy) phenyl] thio ether-bis-N-methyl imide, 2 parts 50% NaOH and 4 parts of water were stirred and refluxed for 24 hours. The methyl amine evolved was allowed to escape into the atmosphere. The mixture was then diluted with an equal volume of water. Sufficient concentrated sulfuric acid having a density of about 1.84 was added slowly to the diluted base solution; while it was stirred the pH of mixture was reduced to 1 based on variable color pH paper. This produced a pasty mixture which was heated. At about 100° C, the pasty mixture solidified giving a readily filterable material. The melting point of the material was 130°–135° with evolution of water. It was obtained in quantitative yield. The product was [4(3,4-dicarboxyphenoxy) phenyl] thio ether.

Although the above examples illustrate only a few of the very many variables to which the present invention can be practiced, it should be understood that the present invention is broadly applicable to the production of aromatic bis(ether dicarboxylic acid)s derived from the base hydrolysis of bisimides of formula (1).

What I claim as new and desire to secure by Letters Patent of the United States is:

1. In a method for making aromatic bis(ether dicarboxylic acid)s involving
   1. hydrolyzing the coresponding aromatic bis (etherimide) with an alkali hydroxide to produce a tetraacid salt base hydrolysis mixture,
   2. acidifying the tetraacid salt by pouring the base hydrolysis mixture into an aqueous solution of a mineral acid to produce a tetraacid acidification mixture, and
   3. effecting the gravity separation of tetraacid from the resulting acidification mixture, resulting in the build up of unrecovered aqueous mineral acid which method for making aromatic bis(ether dicarboxylic acid) involves the improvement comprising, 4. acidifying the aromatic bis(ether diacid) salt by directly adding a concentrated mineral acid to the base hydrolysis mixture at a temperature in the range of from about 15° C to 75° C until the pH of the resulting mixture is reduced to less than about 1,
   5. heating the resultant mixture to a temperature in the range of between 80° C to reflux, and
   6. effecting the separation of the tetraacid from the resulting mixture, whereby the amount of unrecovered aqueous mineral acid in the acidification mixture is substantially reduced.

2. A method in accordance with claim 1, where the mineral acid is sulfuric.

3. A method in accordance with claim 1, where the aromatic bis(etherimide) is 2,2-bis[4(3,4-dicarboxyphenoxy)-phenyl] propane-bis-N-methyl imide.

4. A method in accordance with claim 1, where the aromatic bis(etherimide) is 3,3', 4,4'-tetracarboxydiphenyl ether-bis-N-methyl imide.

5. A method in accordance with claim 1, where the aromatic bis(etherimide) is [4(3,4-dicarboxyphenoxy)-phenyl] thio ether-bis-N-methyl imide.

6. A method in accordance with claim 1, where the tetraacid is recovered by vacuum filtration.

7. A method in accordance with claim 1, where the mineral acid is phosphoric acid.

8. A method in accordance with claim 1, where the mixture is refluxed to crystallize the aromatic bis-(ether dicarboxylic acid) paste.

* * * * *